United States Patent
Hub et al.

(10) Patent No.: US 8,536,379 B2
(45) Date of Patent: Sep. 17, 2013

(54) MANUFACTURE OF TERTIOBUTYL HYDROPEROXYDE FROM RENEWABLE MATERIALS, TERTIOBUTYL HYDROPEROXIDE THUS OBTAINED, AND USES THEREOF

(75) Inventors: Serge Hub, Villeurbanne (FR); Philippe Maj, Brignais (FR)

(73) Assignee: Arkema France, Colombes (FR)

( * ) Notice: Subject to any disclaimer, the term of this patent is extended or adjusted under 35 U.S.C. 154(b) by 248 days.

(21) Appl. No.: 13/121,300

(22) PCT Filed: Sep. 24, 2009

(86) PCT No.: PCT/FR2009/051808
§ 371 (c)(1), (2), (4) Date: Mar. 28, 2011

(87) PCT Pub. No.: WO2010/034941
PCT Pub. Date: Apr. 1, 2010

(65) Prior Publication Data
US 2011/0178324 A1    Jul. 21, 2011

(30) Foreign Application Priority Data
Sep. 29, 2008  (FR) ...................... 08 56515

(51) Int. Cl.
C07C 409/04  (2006.01)
(52) U.S. Cl.
USPC ......................................... 568/568; 568/576
(58) Field of Classification Search
USPC .................................. 568/568, 576
See application file for complete search history.

(56) References Cited

U.S. PATENT DOCUMENTS

| | | | | | |
|---|---|---|---|---|---|
| 2,012,787 | A | * | 8/1935 | Huyser et al. | 558/38 |
| 2,223,807 | A | * | 12/1940 | Milas | 568/558 |
| 2,630,456 | A | * | 3/1953 | Vaughan et al. | 568/568 |
| 3,950,442 | A | | 4/1976 | Vogel et al. | |
| 4,357,479 | A | * | 11/1982 | Imai | 568/899 |
| 4,863,862 | A | * | 9/1989 | Fukuda et al. | 435/166 |
| 2008/0030502 | A1 | | 2/2008 | Chapman | |
| 2008/0033217 | A1 | | 2/2008 | Dakka et al. | |
| 2008/0312485 | A1 | | 12/2008 | Takai et al. | |

FOREIGN PATENT DOCUMENTS

| | | | |
|---|---|---|---|
| EP | 0135295 | A2 | 3/1985 |
| EP | 0501577 | A1 | 9/1992 |
| EP | 0523838 | A2 * | 1/1993 |
| EP | 1953129 | A1 * | 8/2008 |
| JP | S40-02408 | | 2/1966 |

OTHER PUBLICATIONS

Killeffer, D. H. Ind. Eng. Chem. 1927, 19, 46-50.*
Wilkinson et al. J. Bacteriol. 1995, 177, 439-448.*
Merriam-Webster definition for "isolate", obtained from http://www.merriam-webster.com/dictionary/isolate on Mar. 4, 2013.*
English-language translation of the Written Opinion of the International Searching Authority issued May 6, 2011 in PCT/FR2009/051808, 9 pages.
English-language translation of the International Search Report issued Jun. 2, 2010 in PCT/FR2009/051808, 3 pages.
"Research of Biofuel Butanol and its Future" Lin et al., Modern Chemical Industry, (Apr. 2008) pp. 84-87+95 (English language abstract).
Study on the Preparation of tert-butyl Hydroperoxide and di-t-butyl Periode, Yue et al, Applied Chemical Industry, (Jul. 2008) vol. 37, No. 7, pp. 808-810+814 (English language abstract).
"The Role of L-Phenylalanine in the Production of Isobutene by *Rhodotorula minuta*" Fujii et al., Journal of Fermentation and Bioengineering, vol. 67, No. 2, pp. 115-118 (1989).

* cited by examiner

*Primary Examiner* — Joseph Kosack
*Assistant Examiner* — Matthew Coughlin
(74) *Attorney, Agent, or Firm* — Buchanan Ingersoll & Rooney PC

(57) ABSTRACT

The present application relates to a method for manufacturing tert-butyl hydroperoxide that includes the following steps: a) fermenting renewable raw materials and optionally purifying the same to produce a mixture containing at least butanol; b) dehydrating the butanol into butane; c) converting the butane into isobutene and optionally hydrating the isobutene to produce tert-butanol; d) reacting the product of step c) with hydrogen peroxide so as to produce tert-butyl hydroperoxide; and e) isolating the tert-butyl hydroperoxide. The invention also relates to tert-butyl hydroperoxide containing carbon atoms from renewable resources, to the compositions containing said tert-butyl hydroperoxide, and also relates to the use thereof as a polymerization initiator.

9 Claims, No Drawings

MANUFACTURE OF TERTIOBUTYL HYDROPEROXYDE FROM RENEWABLE MATERIALS, TERTIOBUTYL HYDROPEROXIDE THUS OBTAINED, AND USES THEREOF

CROSS-REFERENCE TO RELATED APPLICATIONS

This application is a national stage application under 35 U.S.C. §371 of PCT/FR2009/051808, filed Sep. 24, 2009, which claims benefit to French application FR 0856515, filed on September 29, 2008.

FIELD OF INVENTION

The present invention relates to a process for producing tert-butyl hydroperoxide from renewable starting materials.

In particular, the invention relates to a process for producing tert-butyl hydroperoxide from alcohols resulting from the fermentation of renewable starting materials, the renewable starting materials preferably being plant materials.

BACKGROUND OF THE INVENTION

Tert-butyl hydroperoxide (TBHP), also known as 1,1-dimethylhydroperoxide or 2-hydroperoxy-2-methylpropane, corresponds to the formula:

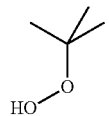

Tert-butyl hydroperoxide is known for its use as a polymerization initiator: under appropriate operating conditions (temperature, redox conditions, etc.), it breaks down to produce free radicals that will generate active sites on the backbone of the compound to be polymerized.

It can also be used as a starting material for the synthesis of other organic peroxides, such as peresters, peroxyacetals or peracetals, dialkyl peroxides or monoperoxypercarbonates.

There are several routes for the synthesis of tert-butyl hydroperoxide from isobutene, isobutane or tert-butanol, these starting materials all being obtained from non-renewable starting materials of fossil (oil) origin.

However, oil resources are limited, and extraction of oil requires digging deeper and deeper and under technical conditions which are increasingly difficult requiring sophisticated equipment and the implementation of processes which are increasingly costly in energy terms. These constraints have a direct consequence on the cost of producing tert-butyl hydroperoxide.

The problem forming the basis of the present patent application is that of proposing other routes for the synthesis of tert-butyl hydroperoxide.

Advantageously and surprisingly, the inventors of the present invention have implemented a process for the industrial production of tert-butyl hydroperoxide from renewable starting materials.

The process according to the invention makes it possible to at least partly do away with starting materials of fossil origin and to replace them with renewable starting materials.

The tert-butyl hydroperoxide obtained according to the process according to the invention is of a quality such that it can be used in all the applications in which it is known practice to use tert-butyl hydroperoxide, even the most demanding applications.

SUMMARY OF INVENTION

A subject of the invention is a process for producing tert-butyl hydroperoxide, comprising the following steps:
  a) fermenting renewable starting materials and, optionally, purifying so as to produce a mixture comprising at least butanol;
  b) dehydrating the butanol to give butene;
  c) converting the butene to give isobutene;
  d) reacting with hydrogen peroxide so as to produce tert-butyl hydroperoxide,
  e) isolating the tert-butyl hydroperoxide.

Step c) can also be followed by a step of hydrating the isobutene to give tent-butanol; according to this variant, in step d), the tert-butanol reacts with the hydrogen peroxide.

Another subject of the invention is the tert-butyl hydroperoxide that can be obtained by means of the process according to the invention.

More generally, a subject of the invention is tert-butyl hydroperoxide obtained from renewable starting materials, i.e. tert-butyl hydroperoxide comprising carbon atoms of renewable origin, i.e. which can be determined according to the standard ASTM D6866.

Another subject of the invention is the uses of the tert-butyl hydroperoxide and the compositions comprising tert-butyl hydroperoxide.

Other subjects, aspects, and features of the invention will emerge on reading the following description.

DETAILED DESCRIPTION OF CERTAIN EMBODIMENTS OF THE INVENTION

Step a) of the process for producing tert-butyl hydroperoxide according to the invention comprises fermenting renewable starting materials so as to produce a mixture comprising at least butanol.

A renewable starting material is a natural, for example animal or plant, resource, the stock of which can be reconstituted over a short period on the human scale. It is in particular necessary for this stock to be able to renew itself as quickly as it is consumed. For example, plant materials have the advantage of being able to be cultivated without their consumption resulting in an apparent decrease in natural resources.

Unlike materials derived from fossil materials, renewable starting materials contain $^{14}C$. All carbon samples drawn from living (animal or plant) organisms are in fact a mixture of three isotopes: $^{12}C$ (representing approximately 98.892%), $^{13}C$ (approximately 1.108%) and $^{14}C$ (traces: $1.2 \times 10^{-10}$%). The $^{14}C/^{12}C$ ratio of living tissues is identical to that of the atmosphere. In the environment, $^{14}C$ exists in two predominant forms: in the form of carbon dioxide ($CO_2$), and in organic form, i.e. carbon integrated into organic molecules.

In a living organism, the $^{14}C/^{12}C$ ratio is kept constant by the metabolism since carbon is continually exchanged with the external environment. Since the proportion of $^{14}C$ is constant in the atmosphere, it is likewise constant in the organism, as long as it is alive, since it absorbs this $^{14}C$ to the same degree as the ambient $^{12}C$. The average $^{14}C/^{12}C$ ratio is equal to $1.2 \times 10^{-12}$.

$^{12}C$ is stable, i.e. the number of $^{12}C$ atoms in a given sample is constant over time. $^{14}C$ is radioactive, the number of $^{14}C$ atoms in a sample decreases over time (t), its half-life being equal to 5730 years.

The $^{14}C$ content is substantially constant from extraction of the renewable starting materials to production of the tert-butyl hydroperoxide according to the invention, and even to the end of the use of said tert-butyl hydroperoxide.

Consequently, the presence of $^{14}C$ in a material, irrespective of the amount, gives an indication as to the origin of the molecules making up said material, that is to say whether they originate from renewable starting materials and not from fossil materials.

The amount of $^{14}C$ in a material can be determined according to one of the methods described in standard ASTM D6866-06 (Standard Test Methods for Determining the Biobased Content of Natural Range Materials Using Radiocarbon and Isotope Ratio Mass Spectrometry Analysis).

This standard comprises three methods for measuring organic carbon resulting from renewable starting materials, known as "biobased carbon". The proportions indicated for the tert-butyl hydroperoxide of the invention are preferably measured according to the mass spectrometry method or the liquid scintillation spectrometry method described in this standard, and most preferably by mass spectrometry.

These methods of measurement evaluate the $^{14}C/^{12}C$ isotope ratio in the sample and compare it with a $^{14}C/^{12}C$ isotope ratio in a material of biological origin giving the 100% standard, in order to measure the percentage of organic carbon in the sample.

Preferably, the tert-butyl hydroperoxide according to the invention comprises an amount of carbon resulting from renewable starting materials of greater than 20%, preferably greater than 50% by weight, relative to the total weight of carbon of the tert-butyl hydroperoxide.

In other wards, the tert-butyl hydroperoxide can comprise at least $0.24 \times 10^{-10}$% by weight of $^{14}C$, preferably at least $0.6 \times 10^{-10}$% by weight of $^{14}C$.

Advantageously, the amount of carbon resulting from renewable starting materials is greater than 60%, preferably greater than 70%, even more preferably greater than 80%.

Use may be made, as renewable starting materials, of plant materials, materials of animal origin or materials of plant or animal origin resulting from recovered materials (recycled materials).

By way of plant materials, there are in particular sugars, starches and also any plant material containing at least sugars and/or starches.

The plant materials containing sugars are essentially sugar cane and sugar beet; mention may also be made of maple, date palm, sugar palm, sorghum or American agave; the plant materials containing starches are essentially cereals and legumes, such as corn, wheat, barley, sorghum, rye, soft wheat, rice, potato, cassava, sweet potato, or else algae.

Among materials resulting from recovered materials, mention may in particular be made of plant or organic waste comprising sugars and/or starches.

Advantageously, low-quality starting materials may be used, for instance potatoes that have been frozen, cereals contaminated with mycotoxins or surplus sugar beet.

Preferably, the renewable starting materials are plant materials.

As renewable starting materials, use may also be made of cellulose and hemicellulose, or even lignin, which, in the presence of suitable microorganisms, can be converted into materials comprising sugar. Among these renewable materials are straw, wood and paper, which may advantageously derive from recovered materials.

The fermentation of the renewable materials is carried out in the presence of one or more suitable microorganisms; said microorganism may optionally have been modified naturally, by a chemical or physical constraint, or genetically, whereupon it is termed a mutant. Conventionally, the microorganism used is a *Clostridium*, it is advantageously *Clostridium acetobutylicum* or a mutant thereof.

The lists presented above are not limiting.

The fermentation step can also be preceded by a step of hydrolyzing the starting materials by means of a cellulase enzyme or of a complex of several cellulase enzymes.

Fermentation generally results in the production of a mixture of products; typically, the production of butanol is accompanied by the production of acetone.

Thus, advantageously, the fermentation step is followed by a step for isolating the butanol.

The butanol generally essentially consists of 1-butanol.

The butanol isolation generally consists in separating the various products of the reaction, for example by heteroazeotropic distillation. This separation may also be followed by a distillation intended to obtain the butanol in a more concentrated form.

Another advantage of the process according to the invention is that it saves energy: the fermentation step and the optional hydrolysis step of the process according to the invention are carried out at low temperatures. Their energy cost is also low compared with the costs of extracting butane or benzene.

This energy saving is also accompanied by a reduction in the amount of $CO_2$ emitted into the atmosphere.

In step b), the butanol is dehydrated to give butene; this reaction is carried out in the presence of a strong acid such as, for example, sulfuric acid ($H_2SO_4$) or phosphoric acid at a temperature of approximately 120° C.

During step c), the butene obtained in step b) is converted to isobutene.

This reaction is carried out by bringing the butene into contact with a tectometallosilicate which has a ferrierite crystalline structure, at a temperature of between 150° C. and 450° C., a butene partial pressure of 0.5 bar and a total pressure of between 0.5 and 25 bar.

By way of tectometallosilicates which have a ferrierite crystalline structure and which can be used in step c), mention is made of the following ferrierites: FU-9, 151-6, Nu-23, ZSM-21, ZSM-35 and ZSM-38. The tectometallosilicates that can be used in step c) contain silicon and at least one element of the group made up of gallium and aluminum; they preferably contain silicon and aluminum. Preferably, the tectometallosilicates are in hydrogen form.

During step d), the isobutene obtained in step c) reacts with hydrogen peroxide ($H_2O_2$) so as to produce tert-butyl hydroperoxide.

This reaction is carried out in the liquid phase, in the presence of sulfuric acid, with continuous and vigorous stirring. Preferably, the reaction temperature is between 30° C. and 75° C. at atmospheric pressure.

Step c) may also be followed by a step of hydrating the isobutene to give tert-butanol; according to this variant, in step d), it is the tert-butanol which reacts with the hydrogen peroxide. The hydration of the isobutene to give tert-butanol is obtained in the presence of dilute sulfuric acid (50% to 65% by weight), or in the presence of acidic ion exchange resins. The reaction of tert-butanol with hydrogen peroxide to give tert-butyl hydroperoxide is carried out under the same conditions as step d) described above.

Step e) of the process concerns the isolation of the tert-butyl hydroperoxide obtained at the end of step d).

An additional advantage of the process implemented in the present application concerns the impurities present in the isobutene used in step d).

According to a conventional route, the isobutene is obtained by cracking and steam cracking naphtha (derived from petroleum). These techniques, in particular steam cracking, make it possible to obtain a $C_4$ fraction comprising isobutene, but also diolefinic compounds and acetylenic compounds such as propyne, vinylacetylene, 1-butyne and 2-butyne.

These diolefinic and acetylenic compounds are capable of initiating polymerization reactions, of contributing to gum formation, of inhibiting active sites of catalysts, and of influencing solvent effectiveness, and it is therefore necessary to separate them from the isobutene.

The isobutene obtained in step c) of the process according to the present invention has the advantage of not comprising such acetylenic compounds; the process according to the invention does not therefore require the implementation of this separation step which can prove to be difficult and expensive.

The present invention relates to the compounds comprising tert-butyl hydroperoxide obtained from materials of renewable origin and to the uses of tert-butyl hydroperoxide obtained from materials of renewable origin.

In particular, the present invention relates to the use of tert-butyl hydroperoxide obtained from materials of renewable origin for the production of peresters, of peroxyacetals or peracetals, of dialkyl peroxides or of monoperoxypercarbonates. These peresters, peroxyacetals or peracetals, dialkyl peroxides and monoperoxypercarbonates can in particular be used as polymerization initiators.

In the production of peresters, mention may be made of the use of the tert-butyl hydroperoxide obtained from materials of renewable origin with:
  neodecanoyl chloride so as to form tert-butyl peroxyneodecanoate; this perester is, for example, sold under the name Luperox 10 by the company Arkema;
  pivaloyl chloride so as to form tert-butyl peroxypivalate; this perester is, for example, sold under the name Luperox 11 by the company Arkema;
  2-ethylhexanoyl chloride so as to form tert-butyl peroxy-2-ethylhexanoate; this perester is, for example, sold under the name Luperox 26 by the company Arkema;
  3,5,5-trimethylhexanoyl chloride so as to form tert-butyl peroxy-3,5,5-trimethylhexanoate; this perester is, for example, sold under the name Luperox 270 by the company Arkema;
  acetic anhydride so as to form tert-butyl peroxyacetate; this perester is, for example, sold under the name Luperox 7 by the company Arkema;
  isobutyryl chloride so as to form tert-butyl peroxyisobutyrate; this perester is, for example, sold under the name Luperox 80 by the company Arkema;
  benzoyl chloride so as to form tert-butyl peroxybenzoate; this perester is, for example, sold under the name Luperox P by the company Arkema;
  neoheptanoyl chloride so as to form tert-butyl peroxyheptanoate; this perester is, for example, sold under the name Luperox 701 by the company Arkema.

In the production of peroxyacetals or peracetals, mention may be made of the use of the tert-butyl hydroperoxide obtained from materials of renewable origin with:
  methyl ethyl ketone so as to form 2,2-di(tert-butylperoxy) butane; this product is, for example, sold under the name Luperox 220 by the company Arkema;
  3,3,5-trimethylcyclohexanone so as to form 1,1-di(tert-butylperoxy)-3,3,5-trimethylcyclohexane; this product is, for example, sold under the name Luperox 231 by the company Arkema;
  ethyl 3-oxobutyrate so as to form ethyl 3,3-di(tert-butylperoxy)butyrate; this product is, for example, sold under the name Luperox 233 by the company Arkema;
  cyclohexanone so as to form 1,1-di(tert-butylperoxy)cyclohexane; this product is, for example, sold under the name Luperox 331 by the company Arkema.

In the production of dialkyl peroxides, mention may be made of the use of the tert-butyl hydroperoxide obtained from materials of renewable origin with:
  n-butyl 4-oxobutyrate so as to form n-butyl 4,4-di(tert-butylperoxy)valerate; this product is, for example, sold under the name Luperox 230 by the company Arkema;
  cumyl peroxide so as to form tert-butyl cumyl peroxide; this product is, for example, sold under the name Luperox 801 by the company Arkema;
  benzene and propylene so as to form 1,4-bis(tert-butylperoxyisopropyl)benzene, 1,3(4)-bis(tert-butylperoxyisopropyl)benzene or 1,3-bis(tert-butylperoxyisopropyl) benzene; these products are sold respectively under the names Luperox 802, Luperox F and Luperox FM by the company Arkema;
  isobutene so as to form di-tert-butyl peroxide; this product is, for example, sold under the name Luperox DI by the company Arkema.

In the production of monoperoxypercarbonates, mention may be made of the use of the tert-butyl hydroperoxide obtained from materials of renewable origin with:
  2-ethylhexyl chloroformate so as to form OO-tert-butyl O-(2-ethylhexyl) monoperoxycarbonate; this product is, for example, sold under the name Luperox TBEC by the company Arkema;
  isopropyl chloroformate so as to form OO-tert-butyl OO-isopropyl monoperoxycarbonate; this product is, for example, sold under the name Luperox TBIC by the company Arkema.

The present invention also relates to the uses of the tert-butyl hydroperoxide obtained from materials of renewable origin, as a polymerization initiator, or else the use of said tert-butyl hydroperoxide in the preparation of a polymerization initiator.

The invention claimed is:

1. A process for producing tert-butyl hydroperoxide from a renewable starting material comprising at least the following steps of:
  a) fermenting a renewable starting material and, optionally, purifying so as to produce a mixture comprising at least butanol;
  b) dehydrating the butanol to form butene in the presence of a strong acid at a temperature of about 120° C.;
  c) converting the butene to produce isobutene, and optionally hydrating the isobutene to produce tert-butanol;
  d) reacting the product of step c) with hydrogen peroxide so as to produce tert-butyl hydroperoxide; and
  e) isolating the tert-butyl hydroperoxide.

2. The process for producing tert-butyl hydroperoxide of claim 1, wherein step c) comprises hydrating the isobutene to produce tert-butanol, and step d) includes reacting the tert-butanol with the hydrogen peroxide.

3. The process for producing tert-butyl hydroperoxide of claim 2, wherein the step of hydrating the isobutene to give tert-butanol of step c) is carried out in the presence of dilute sulfuric acid, or in the presence of acidic ion exchange resins.

4. The process for producing tert-butyl hydroperoxide of claim 1, wherein the renewable starting material is a plant material selected from sugar cane, sugar beet, maple, date palm, sugar palm, sorghum, American agave, corn, wheat, barley, sorghum, rye, soft wheat, rice, potato, cassava, sweet potato, straw, wood, paper and algae.

5. The process for producing tert-butyl hydroperoxide of claim 1, wherein the fermentation step a) is carried out in the presence of *Clostridium acetobutylicum* or a mutant thereof.

6. The process for producing tert-butyl hydroperoxide of claim 1, wherein the fermentation step a) is followed by a step for isolating the butanol.

7. The process for producing tert-butyl hydroperoxide of claim 1, wherein the step c) comprises bringing the butene into contact with a tectometallosilicate which has a ferrierite crystalline structure, at a temperature of between 150° C. and 450° C., at a butene partial pressure of 0.5 bar and a total pressure of between 0.5 and 25 bar.

8. The process for producing tert-butyl hydroperoxide of claim 1, wherein the step d) is carried out in the liquid phase, in the presence of sulfuric acid, with continuous and vigorous stirring, at a reaction temperature of between 30° C. and 75° C. at atmospheric pressure.

9. The process for producing tert-butyl hydroperoxide of claim 1, wherein said strong acid of step b) is sulfuric acid ($H_2SO_4$) or phosphoric acid.

* * * * *